United States Patent [19]

Ritter

[11] Patent Number: 4,909,736
[45] Date of Patent: Mar. 20, 1990

[54] METHOD OF REPAIRING A TOOTH AND APPARATUS THEREFOR

[76] Inventor: Charles H. Ritter, P.O. Box 12126, Tallahassee, Fla. 32317

[21] Appl. No.: 188,067

[22] Filed: Apr. 27, 1988

Related U.S. Application Data

[63] Continuation-in-part of Ser. No. 43,452, Apr. 28, 1987, abandoned.

[51] Int. Cl.$^4$ .............................................. A61C 5/04
[52] U.S. Cl. ..................................... 433/39; 433/226; 433/223; 425/182; 425/57
[58] Field of Search ...................... 433/39, 41, 37, 142, 433/148, 227, 226, 223, 217.1; 264/230, 36; 156/84, 86; 428/181, 182, 57, 66

[56] References Cited

U.S. PATENT DOCUMENTS

| | | |
|---|---|---|
| 2,438,901 | 4/1948 | Coxe ............................ 128/DIG. 18 |
| 2,835,628 | 5/1958 | Saffir ............................. 433/229 X |
| 3,082,531 | 3/1963 | Jacobson . |
| 3,329,143 | 7/1967 | Gordon ....................... 128/DIG. 18 |
| 3,421,222 | 1/1969 | Newman ........................... 433/226 X |
| 4,200,676 | 4/1980 | Caponigro et al. ........... 174/DIG. 8 |
| 4,563,152 | 1/1986 | McClure ............................... 433/39 |
| 4,596,732 | 6/1986 | Diaz .............................. 174/DIG. 8 |
| 4,608,021 | 8/1986 | Barrett ................................ 433/229 |
| 4,695,926 | 9/1987 | McDermott .................. 174/DIG. 8 |
| 4,718,849 | 1/1988 | Von Weissenfluh et al. ......... 433/39 |

Primary Examiner—Larry Jones
Attorney, Agent, or Firm—Shlesinger & Myers

[57] ABSTRACT

The method of repairing a tooth involves positioning a selected medium contiguous a location of the tooth to be repaired, placing a heat-shrinkable overlay around the tooth for covering the selected medium, heating the overlay to a temperature sufficient to cause shrinkage thereof and thereby operating on the medium. The overlay is subsequently removed to expose a repaired tooth requiring little or no additional post-cure finishing.

35 Claims, 2 Drawing Sheets

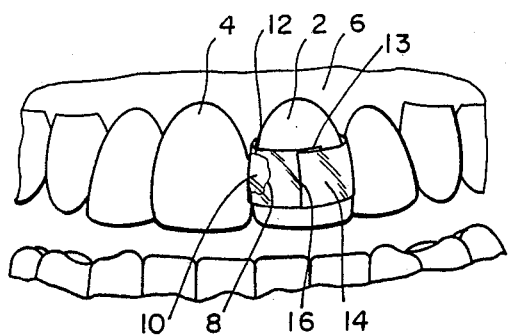
FIG. 1A
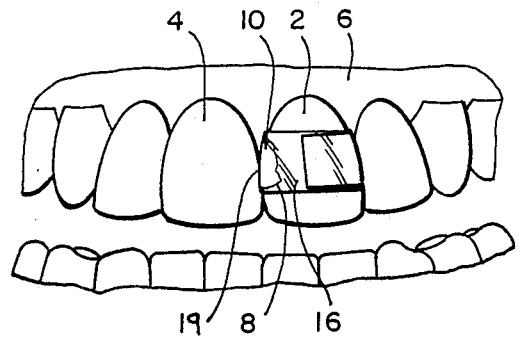
FIG. 1B
FIG. 2
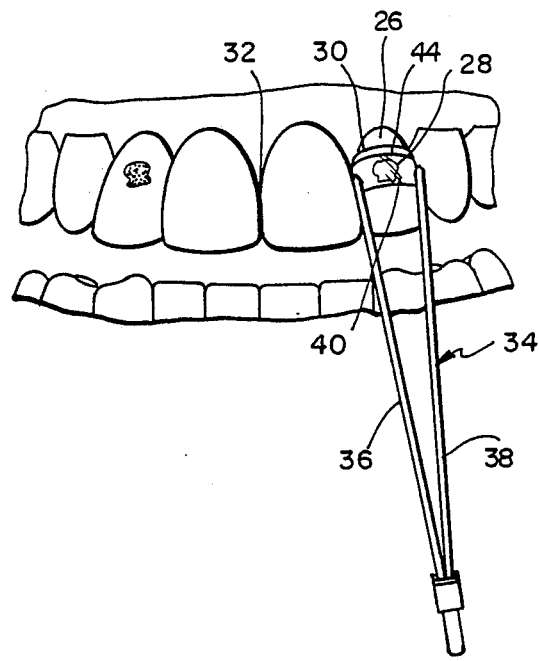
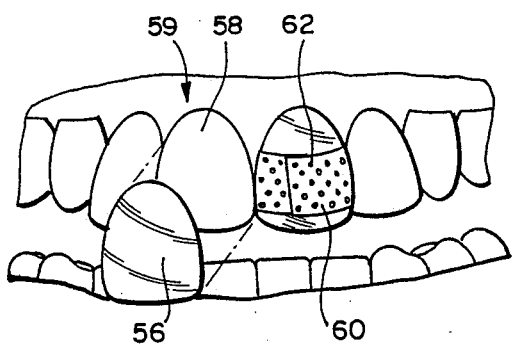
FIG. 3
FIG. 4
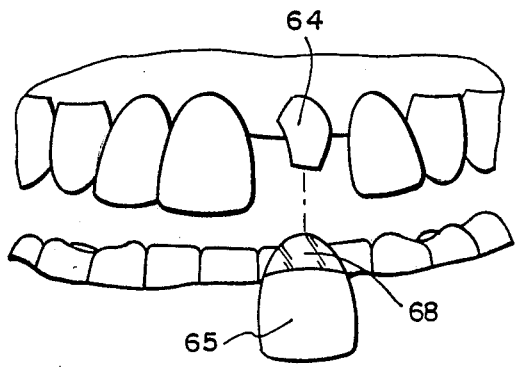

METHOD OF REPAIRING A TOOTH AND APPARATUS THEREFOR

RELATED APPLICATIONS

This is a continuation-in-part of my prior application Ser. No. 043,452, filed Apr. 28, 1987 for METHOD OF REPAIRING A TOOTH AND APPARATUS THEREFOR, now abandoned.

BACKGROUND OF THE INVENTION

In the field of dental medicine, metal amalgams and foils for tooth restoration are giving way to non-metal compositions, such as the composite materials, both light and self-curing. These new restorative materials are advantageous over the prior art metal amalgams in that they are biologically inert, take less time to work with and achieve a more desirable cosmetic effect in terms of matched tooth coloration.

The main drawback with the modern restorative materials is the finishing of the tooth after the material has been cured by polymerization or other chemical reaction. Conventionally, after the tooth has been excavated of the lesion by drilling, the site is isolated with a rubber dam or similar device to insure isolation of the site from any adjacent teeth. The restorative material is then mixed in the proper proportions and inserted into the excavated site. Very often the restorative material is cured by directing a high intensity light beam onto the matrix. It is sometimes necessary to slightly overfill the excavated site with restorative material to insure complete filling with cured material. After curing is complete, the excess material must be removed. Conventionally, the material is removed by manually urging a polishing cloth or the like back and forth until the excess material is removed. Rotary disks and high speed bits compromise the integrity of the surface and are, at best, time consuming. Sanding strips, frequently used, may break upon being inserted between the teeth. Further, excessive force used when inserting a strip may cause trauma to the gingival region near the base of the tooth, thereby causing hemorrhage to the tissue.

Numerous prior art devices exist which attempt to aid in the sanding and finishing of restorative materials. U.S. Pat. No. 4,563,152 to McClure discloses a flexible sanding device for curable dental restorations comprising a flexible strip having an abrasive surface on one side thereof. U.S. Pat. No. 2,090,904 to Singer discloses an H-shaped, resilient dental matrix adapted for being placed between adjacent teeth. U.S. Pat. No. 4,569,342 to Von Nostitz and U.S. Pat. No. 4,413,979 to Ginsburg disclose dental impression trays constructed of plastic material which may be softened at relatively low temperature.

The aforementioned prior art devices either provide a barrier between teeth while filling a tooth with restorative material or provide a sanding strip for positioning around the tooth to etch away excess restorative material after curing. None of the prior art patents discloses a method of finishing the restorative material either before or during the curing of the restorative material. Accordingly, such a method and appropriate apparatus would result in increased efficiency and reduced trauma to surrounding teeth.

OBJECTS AND SUMMARY OF THE INVENTION

The primary object of the disclosed invention is a method for repairing a tooth whereby little or no post-cure finishing is required of the restorative material.

Another object is to provide a method for repairing a tooth whereby the non-metallic dental restorative material may be cured and finished simultaneously, thereby resulting in a more efficient procedure.

A further object is to provide a method of repairing a tooth whereby trauma to the tooth being repaired and associated teeth and gums is reduced.

An additional object of this invention is to provide a uniform, high quality finishing procedure for a non-metallic dental restorative material.

These and other objects of this invention will become apparent from the following description and claims.

DESCRIPTION OF THE DRAWINGS

In the accompanying drawings, which illustrate by way of example a preferred embodiment of this invention:

FIGS. 1 A and B illustrate the treatment of a type III carious lesion, located on the mesial surface of a maxillary central incisor according to the present invention both before and after curing;

FIG. 2 illustrates a class V cavity, located close to the gum line on the front surface of a maxillary central incisor, being treated according to a second embodiment of this invention;

FIG. 3 illustrates a fourth embodiment of the present invention whereby pre-fab composites, porcelain or ceramic veneers may be applied to the front surface of a tooth;

FIG. 4 illustrates a fifth embodiment of the present invention as applied to temporary crown applications;

DETAILED DESCRIPTION OF THE PREFERRED EMBODIMENT

Figure 5:
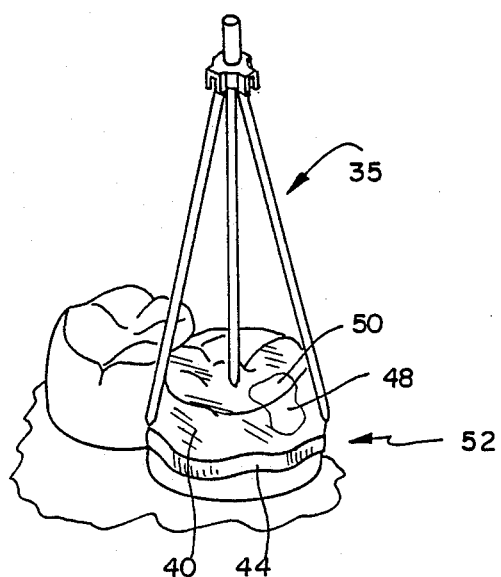
FIG. 5 illustrates a class I, II and III lesion along the side and top of a tooth being treated according to a third embodiment of this invention.

A pair of maxillary central incisor teeth 2 and 4 and an associated gum 6 are illustrated in FIGS. 1 A and B. As best shown in FIG. 1 A, a class III carious lesion, that is, a cavity extending between the teeth, has been opened or excavated with a drill bit and the decayed material removed. The cavity has been conventionally extended with further drilling to a preparation or shape generally shown at 8.

After site preparation is complete, the site 8 is washed and dried of any debris and a quantity of soft, uncured restorative material 10 is packed into the prepared site 8 with an appropriate dental instrument. It is necessary to slightly overfill the site 8 with the restorative material 10 to insure complete filling. This overfill results in a small ridge 12.

Prior to curing of the restorative material 10, a strip of heat shrinkable overlay 14 is wrapped around tooth 2 so as to overlie the uncured restorative material 10. The heat shrinkable overlay 14 is, preferably, a light-transmissive polymeric sheet comprised of polyvinyl chloride or the like. However, any of the polymeric based heat shrinkable films known in the art are adaptable and contemplated within the present invention, and the example cited herein is not in any way intended to limit the present invention.

End portion 16 of the heat shrinkable overlay 14 is secured onto the underlying film 13 by cement or like adhesive. The present invention is not intended to be limited to any particular type of adhesive, or any particular manner of application thereof, whether prior to or after the overlay 14 is wrapped.

After the heat shrinkable overlay 14 has been secured at its end portion 16, the overlay 14 is heated to effect shrinkage of the film 14 around the tooth 2, and thereby against the uncured restorative material 10. A forced air type heater is preferred, and includes a device similar to a conventional hair dryer. The heater should produce an even flow of substantially constant temperature heated air. Preferably, the air temperature can be adjusted as may be required. I have found that heating by this means is not irritating to the patient and achieves uniform heating of the overlay 14. Heated air may be directed from the device through a narrow funnel or similar device so that the air is concentrated at a particular location of the mouth, i.e. the tooth to be repaired.

Heating is effected for a period of time sufficient to cause the overlay 14 to sufficiently shrink and thus tighten around the tooth 2 and the associated uncured restorative material 10, as can be best seen in FIG. 1 B. Heating, and thereby shrinkage, forces the overlay 14 into a tight relationship against the natural contours of the tooth 2. Consequently, the uncured, softened restorative material 10 is squeezed and achieves a natural contour corresponding substantially to that of the tooth 2. The ridge 12, formed from the initial packing of the restorative material 10, is automatically finished by the heat caused shrinkage forces, thereby eliminating much or all post-cure finishing.

The restorative material 10 may be conventionally cured after sufficient shrinkage. A high intensity beam of light is directed upon the tooth 2, either during or immediately after the above described heat shrink step. The heat shrinkable overlay 14 is transparent, thereby permitting light to readily pass therethrough so as to cure the restorative material 10. The overlay 14 need not be removed during the cure step. The restorative material 10 may be self curing, thereby gradually hardening without any additional treatment and even avoiding the need for light application. The heat-shrunk overlay 14 may then be removed from the tooth 2 to expose the finished restorative surface 19.

Figure 6:
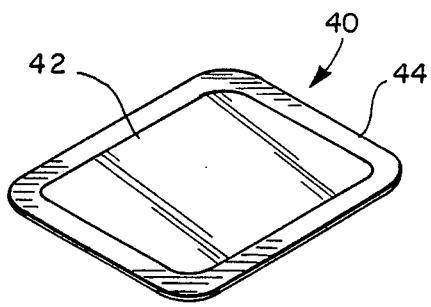
FIG. 6 illustrates a heat shrinkable clear polymeric sheet having a pliable non-shrink border material for use as an overlay.

FIG. 2 illustrates the invention as directed to class V cavities which are situated above the gum-line. The tooth 26 to be repaired is prepared by first drilling out the carious lesion, as previously described, to leave a convex site 28 for receipt of restorative material 30. Because the cavity is located above the lower edge of the gum line 32, the previously described heat shrinkable overlay cannot be wrapped around the tooth 26. Instead, a caliper device 34, having extensions 36 and 38, urges a heat shrinkable overlay 40 against the tooth 26. As best shown in FIG. 6, the heat shrinkable overlay 40 comprises a light transparent heat shrinkable film 42, of composition substantially the same as overlay 14, having a border material 44 which is pliable but which is not heat shrinkable. Examples of such border materials are metals, such as aluminum foil, or any shapable celluloid material which is readily securable to the heat shrinkable film.

Referring again to FIG. 2, the heat shrinkable overlay 40 is urged into engagement with the front surface of the tooth 26 and the soft, uncured restorative material 30 by caliper device 34. The pliable border material 44 is likewise urged against the surface of the tooth 26 in a molded fashion to further effect contact with the tooth 26. The heat shrinkable film 40 may now be heated to effect shrinkage, followed by curing of the restorative material 30.

As best shown in FIG. 5, a class I, II and III type filling is positioned upon the top, side and incisal edge of a tooth. A multiprong caliper device 35 positions a heat shrinkable overlay 40 having the pliable border material 44 incorporated therein. It should be noted that in this application, the restorative material 48 may be located on the top 50 of the tooth. A patient must gently "bitedown" onto the uncured restorative material 50 so as to yield a proper surface between the tooth 52 and its upper matching tooth (not shown). The amount of border material 44 may be increased while the heat shrinkable film or "shrink window" 42 may be decreased in size. This permits increased molding along the sides of the tooth because the increased border material 44 provides an appropriate "shrink window" 42 to allow sufficient light to reach the restorative material on the top 50 of the tooth. The multiprong caliper device 35 urges the heat shrinkable overlay 40 against the sides and the top 50 of the tooth 52. The overlay 40 and the restorative material 48 are heated as outlined above, followed by removal of the overlay 40 for exposure of the finished tooth 52.

Turning now to FIG. 3, it can be seen that preformed veneers 56 may similarly be applied to the front surface of a tooth 58 according to the present invention. The preformed tooth-like veneer may be a composite or porcelain structure, or any of the currently available materials used in such applications. A properly sized preformed veneer 56 is matched in shape and color with the front surface 58 of the tooth. The veneer 56 is coated with a self-cure or light curable glue or adhesive. The veneer 56 is applied to the etched surface of the tooth 59 and a shrink wrap overlay 60 is then wrapped around the veneer 56 and tooth 59. The shrink wrap overlay 60 is similar to those previously described and further includes a series of perforations 62 extending through the overlay 60. The edge of the uncured overlay 60 is attached by an adhesive or other means as indicated above. Upon heat curing of the overlay 60, the preformed veneer 56 is forced against the front surface 58 of the tooth 59 and excess adhesive exits through the perforations 62 of the shrink wrap overlay 60. The heat treated overlay 60 is then removed to expose a finished pre-formed veneer requiring little or no additional treatment.

FIG. 4 illustrates the invention as applied to temporary crow applications. A tooth is reformed by drilling to yield a suitable base 64 for temporary crown 65 which further includes a shrink wrap portion 68. After applying glue or any similar type adhesive used in such applications to the interior of the temporary crown 65, it is urged against the base portion 64. The shrinkage provides not only a better fit for crown 56, but improved cosmetic appeal because the shrink wrap portion 68 is closely urged near the gum line.

Figure 7:
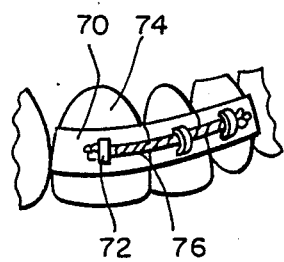
FIG. 7 illustrates a sixth embodiment of the invention for use in the orthodontic field of dentistry.

FIG. 7 illustrates an adaptation of the present invention to the field of orthodontic dentistry. A series of conventional bands 70 with attached loops 72 are secured to a series of individual teeth 74 by cementing or the like. The heat shrinkable overlay material outlined above is formed into an elongated strand 76 and is threaded through the loops 72 of the band 70. The strand 76 is readily secured to each of the loops 72. When the orthodontist heats the elongated strand 76, the strand shrinks a sufficient amount, thereby urging the associated bands 70 together. The bands 70 can thus be adjusted by periodic heating of the elongated strand 76. This method of adjustment eliminates the need for extending and manipulating a conventional wire by a trained Orthodontist. Routine tightening can be effected by the patient himself in the convenience of his own home.

Figure 8:
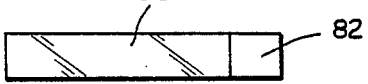
FIG. 8 is an elevational view of an overlay pursuant to the invention.
Figure 9:
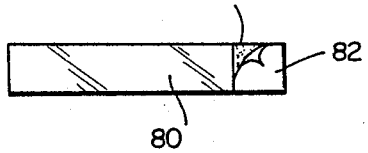
FIG. 9 discloses the overlay of FIG. 8 with the adhesive exposed.

FIG. 8 discloses transparent overly 80 to which silicone coated release strip 82 has been applied. Underlying the release strip 82 is pressure sensitive adhesive 84, as best shown in FIG. 9, in order to permit one end of the overlay 80 to be secured to an underlying portion, such as with the overlay 14 of FIGS. 1 A and 1B.

The release strip 82 is, preferably, colored in order to permit easy identification. Similarly, the adhesive 84 may be colored in order to facilitate positioning of the end thereof on an underlying portion. While the adhesive 84 is disclosed as being of the pressure sensitive type, other types of adhesive are usable.

While this invention has been described as having a preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention of the limits of the appended claims.

What I claim is:

1. A method of repairing a tooth, comprising the steps of:
  (a) positioning a selected medium contiguous a location of a tooth to be repaired;
  (b) placing a heat-shrinkable overlay around the tooth and covering the positioned medium;
  (c) heating the overlay to a temperature sufficient to cause shrinkage thereof so that the overlay operates on the medium; and,
  (d) removing the overlay.

2. The method as in claim 1, including the step of:
  (a) curing the medium with light prior to removal of the overlay.

3. The method as in claim 1, including the steps of:
  (a) preparing the location by drilling a portion of the tooth; and,
  (b) packing the drilled portion with the selected medium.

4. The method as in claim 3, including the step of:
  (a) selecting the medium from the group consisting of restorative, curable materials.

5. The method as in claim 3, including the step of:
  (a) curing the selected medium after heat shrinking the overlay.

6. The method as in claim 1, including the step of:
  (a) providing an overlay which is a polymeric material.

7. The method as in claim 6, including the step of:
  (a) providing an overlay which is polyvinyl chloride.

8. The method as in claim 6, including the step of:
  (a) providing an overlay which is a clear, polymeric sheet having a pliable, non-shrink border material.

9. The method as in claim 8, including the step of:
  (a) providing a border material which is metallic.

10. The method as in claim 8, including the step of:
  (a) providing a border material which is a celluloid material.

11. The method as in claim 8, including the step of:
  (a) holding the overlay at least partially around the sides and top of the tooth with a multi-pronged caliper means prior to heating.

12. The method as in claim 1, including the step of:
  (a) providing an overlay which is a cellulosic laminate.

13. The method as in claim 1, including the step of:
  (a) providing an overlay having adhesive means at an end portion thereof.

14. The method as in claim 13, including the step of:
  (a) providing an overlay having a removable release strip overlying the adhesive means.

15. The method as in claim 13, including the step of:
  (a) providing an overlay having an adhesive end portion which is of a color differing from that of the overlay.

16. The method as in claim 1, including the step of:
  (a) heating the overlay with forced, warm air.

17. The method as in claim 1, including the step of:
  (a) holding the overlay against the tooth with a multi-pronged caliper means prior to heating.

18. The method as in claim 1, including the step of:
  (a) providing a veneer as the selected medium.

19. The method as in claim 18, including the step of:
  (a) providing veneer selected from the group consisting of porcelain and acrylic.

20. The method as in claim 18, including the steps of:
  (a) adhesively securing the veneer to the tooth;
  (b) providing a perforated overlay; and,
  (c) forcing excess adhesive through the perforations during heating of the overlay.

21. The method as in claim 20, including the step of:
  (a) curing the adhesive after heating of the overlay material.

22. The method as in claim 1, including the step of:
  (a) providing a selected medium which has the overlay incorporated therein.

23. The method as in claim 22, including the step of:
  (a) providing the selected medium as a dental crown having an overlay skirt portion formed contiguous with an opening extending therein.

24. A dental overlay device, comprising:
  (a) a length of heat shrinkable light transmissive polymeric material of a selected length;
  (b) adhesive means coating an end portion of said length;
  (c) a pliable, non-shrink border material secured about said length.

25. The overlay of claim 24, wherein:
  (a) said boarder material is metal.

26. The overlay of claim 25, wherein:
  (a) said metal is aluminum.

27. The overlay of claim 24, wherein:
  (a) said border material is cellulosic.

28. The overlay of claim 24, wherein:

(a) a removable release strip covering said adhesive means.

29. A dental overlay device, comprising:
(a) a length of heat shrinkable material of selected length having an adhesive coated end portion; and,
(b) a series of perforations extending through said length.

30. The overlay of claim 29, wherein:
(a) said material is light transmissive and polymeric.

31. The overlay of claim 29, wherein:
(a) a removable release strip covers said adhesive.

32. The overlay of claim 29, wherein:
(a) said end portion is colored differently than is said length.

33. The overlay of claim 29, wherein:
(a) said adhesive is colored differently than is said length.

34. A dental overlay device, comprising:
(a) a length of heat shrinkable material of selected length having an adhesive coated end portion; and,
(b) said end portion is colored differently than is said length.

35. The overlay of claim 34, wherein:
(a) a removable release strip covers said adhesive.

* * * * *